(12) United States Patent
Gossen et al.

(10) Patent No.: US 7,911,215 B2
(45) Date of Patent: Mar. 22, 2011

(54) TEST PATCH SYSTEM AND METHOD (75) Inventors: Paul Gossen, Louisville, KY (US);
Jayant Angal, Louisville, KY (US);
Matthew K. Musho, York, PA (US);
Joseph E. Yates, Crestwood, KY (US)

(73) Assignee: Innovative Productivity, Inc., Louisville, KY (US)

( * ) Notice: Subject to any disclaimer, the term of this patent is extended or adjusted under 35 U.S.C. 154(b) by 431 days.

(21) Appl. No.: 12/172,329

(22) Filed: Jul. 14, 2008

(65) Prior Publication Data
US 2009/0015273 A1 Jan. 15, 2009

Related U.S. Application Data (60) Provisional application No. 60/949,737, filed on Jul. 13, 2007.

(51) Int. Cl.
*G01R 27/08* (2006.01)
*G01N 27/06* (2006.01)

(52) U.S. Cl. .......................................... 324/693; 73/104

(58) Field of Classification Search .................. 324/693, 324/691, 649, 600, 425, 437, 438, 439, 555, 324/76.11; 436/174, 177–180; 73/104, 863, 73/864
See application file for complete search history.

(56) References Cited

U.S. PATENT DOCUMENTS

| 3,800,219 | A | * | 3/1974 | Fosberg ........................ 324/693 |
| 4,597,942 | A | | 7/1986 | Meathrel |
| 4,719,441 | A | | 1/1988 | Horn |
| D342,321 | S | | 12/1993 | Bresle |
| 5,888,758 | A | | 3/1999 | Wu |
| 5,942,186 | A | | 8/1999 | Sanada et al. |
| 5,958,340 | A | | 9/1999 | Meyer et al. |
| 6,090,475 | A | | 7/2000 | Robinson et al. |
| 6,159,743 | A | | 12/2000 | Johnson et al. |
| 6,425,997 | B1 | | 7/2002 | Johnson |
| 6,501,002 | B1 | | 12/2002 | Roe et al. |
| 6,551,837 | B1 | | 4/2003 | Johnson et al. |
| 6,636,031 | B1 | * | 10/2003 | Kenmochi et al. ......... 324/158.1 |
| 6,819,120 | B2 | | 11/2004 | Tam |
| 6,828,808 | B2 | | 12/2004 | Srinivasan et al. |
| 6,843,354 | B2 | | 1/2005 | Dittmer et al. |
| 6,946,844 | B1 | | 9/2005 | Colahan et al. |
| 7,024,921 | B2 | * | 4/2006 | Sutton ........................... 73/54.04 |
| 7,308,822 | B2 | * | 12/2007 | Sutton ............................. 73/104 |
| 2003/0040682 | A1 | | 2/2003 | Tapper |

FOREIGN PATENT DOCUMENTS

SE 350777 11/1972

* cited by examiner

*Primary Examiner* — Hoai-An D Nguyen
(74) *Attorney, Agent, or Firm* — Alexander P. Brackett; Middleton Reutlinger (57) ABSTRACT

A test system for taking a sample of a constituent on a surface utilizing a fluid source includes a transition region having a capillary layer for delivering a fluid from said fluid source, an extraction region having a collection material in contact with said surface, and a collection region having a sensor reservoir therein for collecting the fluid for analysis.

22 Claims, 6 Drawing Sheets

TEST PATCH SYSTEM AND METHOD

CROSS-REFERENCE TO RELATED APPLICATIONS

This application claims the benefit of U.S. Provisional Patent Application Ser. No. 60/949,737 filed Jul. 13, 2007 and entitled "Test Patch System and Method".

The U.S. Government has a paid-up license in this invention and the right in limited circumstances to require the patent owner to license others on reasonable terms as provided for by the terms of contract no. N00167-07-C-0008 awarded by the U.S. Department of the Navy.

BACKGROUND OF THE INVENTION

1. Field of the Invention

The present invention relates generally to a system for surface contaminant testing and more specifically to a system and method for testing a surface for at least one property such as pH, the presence of chlorides, or conductivity as a measure of the efficacy of a surface treatment applied to said surface.

2. Description of the Related Art

In industrial applications where the treatment of surfaces with protective coatings is regularly used, it is often necessary to test various portions of the treated surfaces to determine whether the protective coating has been properly applied. Alternatively, prior to the treatment of, for example, steel surfaces, the surfaces must be thoroughly cleaned of contaminants and salts such as chloride salts so that corrosion doesn't occur under a treated or painted surface. Accordingly, there are various and sundry prior art systems for determining the presence of contaminants of various types on surfaces.

As one example, chloride ion contamination on steel surfaces is a widespread problem in the shipbuilding industry. Chloride ion contamination is caused by the proximity of steel to ocean air and water, as well as less obvious causes such as salt treatment of icy roads in proximity to the untreated material. Corrosion can occur quite rapidly after a surface is contaminated and as such, surfaces must be cleaned, tested and treated quickly in order to avoid the deleterious effects which will eventually appear when a contaminated surface is treated or coated. Furthermore, painting over a chloride contaminated surface causes failure in immersion service materials such as ballast tanks and the like which of course carries an enormous inconvenience and expense to repair.

Many prior art devices capable of testing surfaces for various properties such as salinity, pH, or conductivity are typically complex and labor intensive assemblies that require a multiplicity of steps in order to accomplish the surface testing. In one popular example, a Bresle patch or sampler has been used as a means for measuring chloride contamination on treated surfaces. The Bresle patch comprises a latex membrane and a foam rubber gasket that creates a water tight sample extraction pocket in contact with a surface when a foam rubber gasket is secured to the surface via an adhesive. The watertight sample extraction pocket is then filled with distilled or deionized water, typically by use of a syringe. After agitating the water by rubbing the patch for a short time period, the water is removed, typically through a syringe or the like, then analyzed by chemical reagents for a constituent property such as chloride ion content. The chemical analysis is typically done by using a "kit" supplied with reagents and instructions for use. The extracted water may also be analyzed for other properties such as pH, electrical conductivity, or the presence of chloride ions using conventional known-in-the art meters designed for those purposes.

Other methods of testing a surface for a constituent property are also known in the art but each of them requires a large amount of time and energy to collect and analyze a single sample. In many prior art systems, various syringes, bottles of water and reagents, surface test patches and other equipment must be coordinated and assembled in an inhospitable industrial fabrication environment. These prior art methods are quite disadvantageous when testing large surface areas, since samples must be collected at many points around the area being treated in a short time before surface treatment can proceed.

Accordingly, there is a need in the art for a system and method of testing for a constituent property of a surface that is capable of being conducted repeatedly and quickly by a user while yielding consistently accurate results.

DETAILED DESCRIPTION OF THE PREFERRED EMBODIMENT(S)

Referring now to FIGS. 1-5 and in accordance with one embodiment of the present invention, a test patch system 10 for testing a surface 2 for the presence of a constituent property comprises a solvent 3 supply ampoule 20, and a test patch 100 comprising a transition region 150, an extraction region 200 and a collection region 250. Surface 2 may be any one of a plurality of surfaces on which a constituent may be present. In one embodiment of the present invention, surface 2 comprises a metal surface, used for example as a component of a marine vessel. In this exemplary embodiment of the invention 10, the constituent to be detected may be a chloride, which may have deleterious effects on an unpainted or coated surface, and which must be removed prior to painting or coating to prevent the ultimate failure of the coating.

Ampoule 20 contains a supply of a solvent 3, such as distilled water 3 used to saturate a media for extracting the constituent, as will be discussed further below. The distilled water 3 (or other solvent as required by an individual application) contained in ampoule 20 remains separated from system 100 by a membrane 22 or stopper disposed proximate an outlet area of ampoule 20 until the system is ready to be used. The membrane 22 of ampoule 20 may be pierced by an end portion 152 of transition region 150 when system 10 is ready for use. In one embodiment of the present invention, end portion 152 may be shaped or narrowed to a point to facilitate the piercing of membrane 22. Alternatively, membrane 22 may be designed to rupture to release water into transition region 150 when ampoule 20 is pressurized by, for example, squeezing.

In a yet further embodiment of the invention, a foam stopper 58 or the like may be included in an outlet portion of ampoule 20, or in transition region 150, that is ruptured or opened upon engagement of ampoule 20 with transition region 150 end portion 152. Furthermore, it should be noted that ampoule 20 may be provided as a separate and distinct component to system 10, such that a variety of different ampoules 20 may be employed in conjunction with the invention by inserting ampoule 20 onto or into end portion 152 of transition region 150.

Test patch 100 may comprise a backplane 110 upon which the components of patch 100 are mounted or assembled. Backplane 110 may comprise a watertight layer, which in an exemplary embodiment is formed of polycarbonate material. Backplane 110 may extend substantially the entire length of test patch system 10 for both ease of assembly, and to provide a substrate for the mounting and positioning of the remaining elements of system 110, as discussed in detail below.

Figure 1:
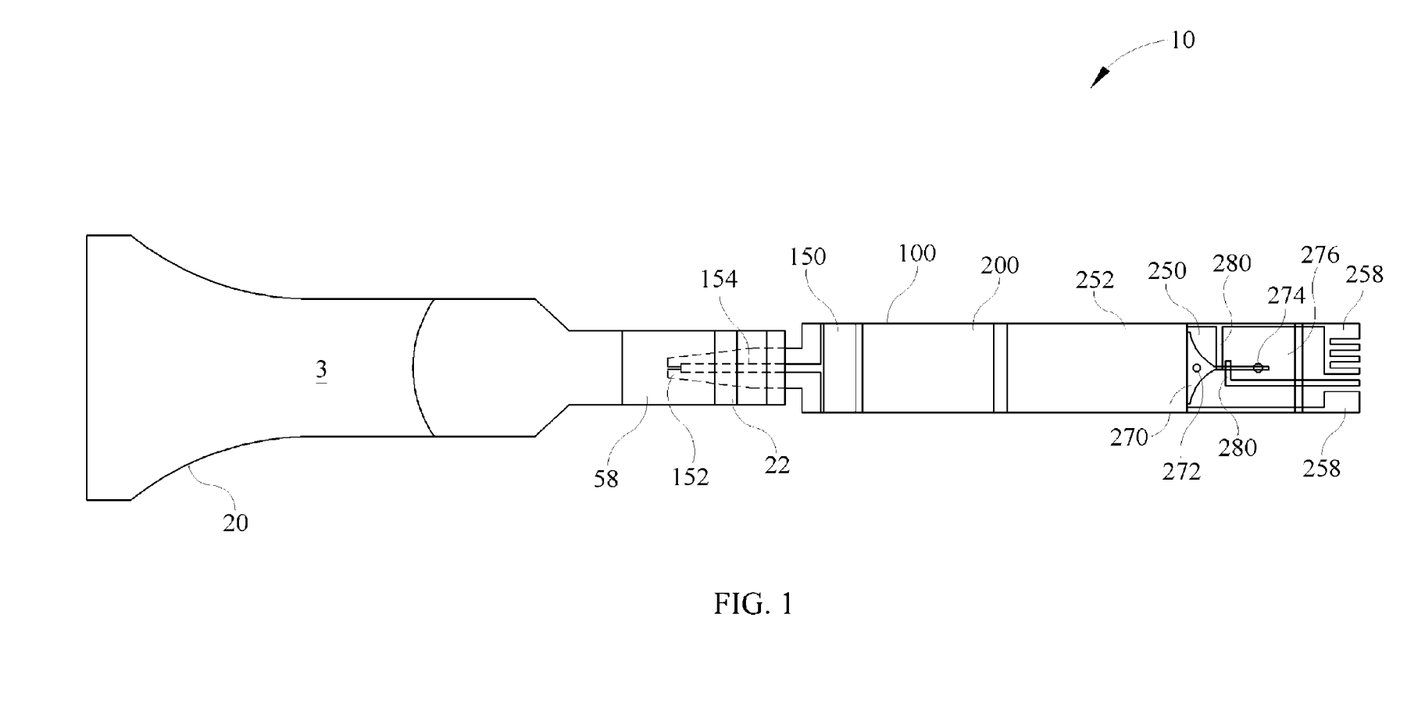
FIG. 1 is a plan view of a test patch system in accordance with one embodiment of the present invention.
Figure 4:
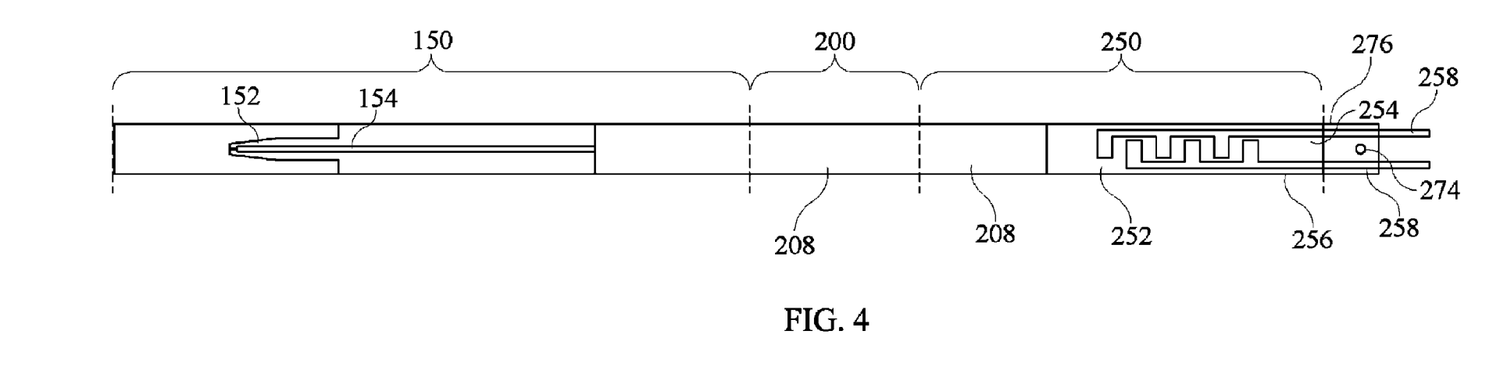
FIG. 4 is a top schematic view of a test patch system in accordance with one embodiment of the present invention.
Figure 5:
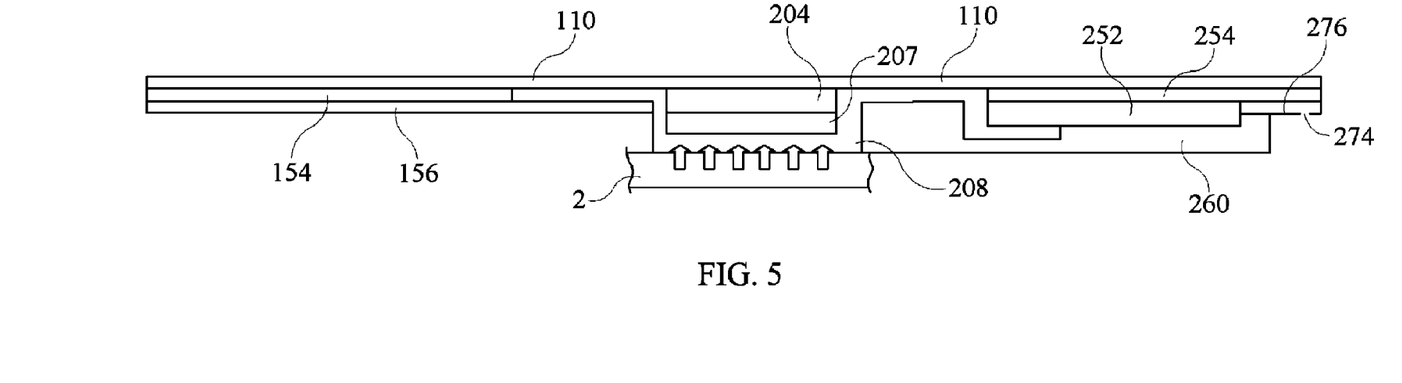
FIG. 5 is a side schematic view of a test patch system in accordance with one embodiment of the present invention.

Referring now to FIGS. 1, 4 and 5 transition region 150 may comprise a plurality of layers. Backplane 110 is secured to capillary plastic layer 154 that is designed to transport water from ampoule 20, through transition region 150 and into extraction region 200. Additionally, a sipper lid 156, formed of a watertight plastic material, is provided as a layer covering capillary layer 154 such that capillary layer 154 is enclosed on the top and bottom by backplane 110 and sipper lid 156. Accordingly, water 3 must flow from ampoule 20 through capillary layer 154 thence into extraction region 200. The fluid flow dynamics of the present invention are best viewed with reference to FIGS. 4 and 5, which depict schematically the component layers of the invention 10 and their interconnections.

Figure 2:
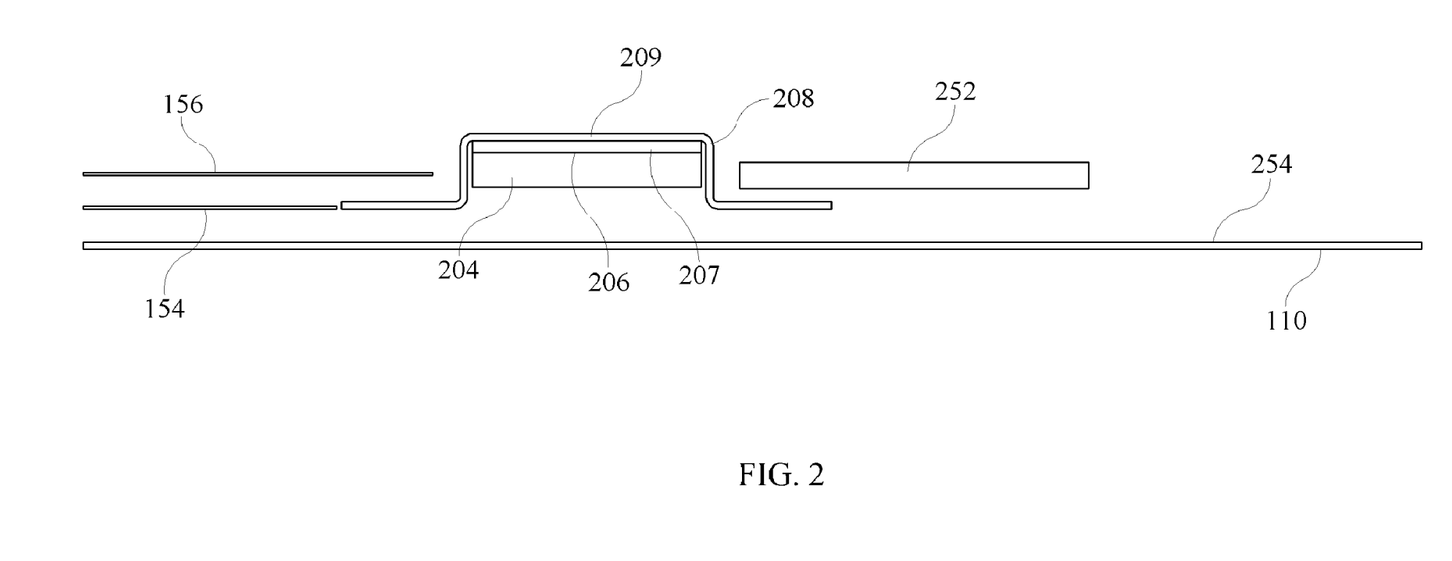
FIG. 2 is an exploded elevation view of a test patch system in accordance with one embodiment of the present invention.
Figure 3:
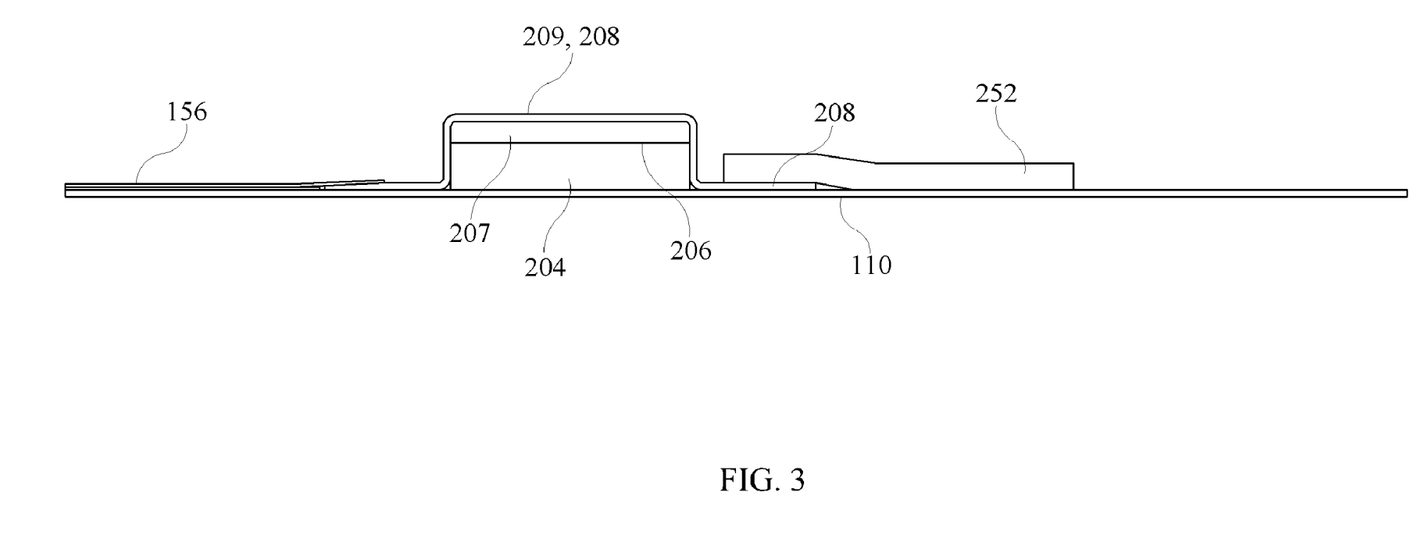
FIG. 3 is an elevation view of a test patch system in accordance with one embodiment of the present invention.

Transition region 150 connects to and abuts extraction region 200 as seen in FIGS. 1, 2 and 3 through a plurality of component layers. As best seen in FIGS. 1 and 2, the demarcation between transition region 150 and extraction region 200 is not at a single layer or surface, but rather is a transition through a plurality of material layers.

Extraction region 200 comprises backplane layer 110, which provides an upper patch surface that is oriented away from the surface 2 being tested. Furthermore, backplane layer 110 provides structural support for the transition region 150, the extraction region 200, and the collection region 250 and their dimensional relationship to each other. Adjacent to backplane 110 in extraction region 200 is a is a watertight closed cell foam layer 204 having an adhesive layer 206 thereon, which secures a flexible, watertight support layer 207. Support layer 207 may be comprised of, for example, a 0.010" thick polycarbonate plastic. Support layer 207 is adjacent and connected to a sample collection material 208 which is comprised of a pad of absorbent fibers which provides a flow path for water 3 entering collection material 208 defined by the orientation of the fibers therein. As long as material 208 and reservoir 252 are not both completely saturated with water 3, material 208 provides a defined flow path for water 3 while preventing water 3 leakage from side portions of material 208. Additionally, collection material 208 comprises a contact region 209 that covers a predetermined surface area of the surface 2 being tested.

Support layer 207 may completely cover the adjacent surface of collection material 208 and be in intimate contact therewith. Additionally, an adhesive layer may be provided between collection material 208 and support layer 207 to maintain intimate contact between the two layers. In a yet further embodiment of the present invention, contact between support layer 207 and collection material 208 is maintained by installing collection material 208 tightly stretched across support layer 207 and securing it thereto with an adhesive, or alternatively by mechanical compression where collection material 208 contacts backplane 110 at either end of extraction region 200.

Foam layer 204 is compressible but resilient to resist compressive forces. Stated another way, foam layer 204 may be elastic in nature. Additionally, since support layer 207 is flexible, foam layer 204 and support layer 207 work in concert to assure that, when collection material 208 is in contact with a sample surface and pressure is applied to backplane 110 proximate extraction region 200, collection material 208 conforms to a plurality of surface geometries while maintaining contact between material 208 contact region 209 and surface 2. In this fashion rough, uneven, curved, flat of irregular surfaces often found in many surface testing environments environments, such as untreated steel, boat hulls, pipes etc. may be accurately tested since the contact region 209 (and thus the predetermined contact area) is maintained over a broad variety of surfaces 2. The invention is therefore capable of maintaining a reproducible contact area between patch 10 and surface 2 which enables the accurate determination of, for example, the concentration of a mass of contaminant in a predetermined unit area.

Sample collection material 208 may comprise a plurality of materials that are capable driving the capillary flow of water 3 through said material 208 while simultaneously extracting salts or other constituents from surface 2 in contact with contact region 209. In one embodiment of the present invention, collection material 208 comprises a layer or layers of absorbent fiber material that provides a flow transport mechanism from sample surface 2 to collect a constituent sample. Other exemplary collection materials 208 include various sponge-like materials, felt fiber mats, paper fiber mats, or spun fiber mats made from synthetic or natural materials that provide a suitable capillary force or action to draw the water solvent 3 across extraction region 200 while keeping water in continuous contact with the surface and that are suitable for conforming to rough uneven surfaces. Collection material 208 is in fluid communication with capillary layer 154 such that material 208 is saturated with distilled water supplied by ampoule 20. Collection material 208 may have capillary and surface tension properties that enable solvent 3 (which in one embodiment is de-ionized water) to be wicked through collection material 208 to contact surface 2 through contact area 209, and further prevents solvent 3 from exiting or leaking from the edges of collection material 208. Accordingly, collection material 208 may have a plurality of capillary fibers oriented from transition region to collection region 250, to inhibit this aforementioned solvent 3 loss.

Additionally, collection material 208 may be comprised of absorbent fibers or equivalent materials which permit fluid 3 flow from a front portion of collection material 208 (that portion proximate transition region 150) to a rear portion thereof (that portion proximate collection region 250) and to and from any area of said surface 2 that is in contact with collection material 208, while preventing fluid 3 escaping from the sides of collection material 208 and from the perimeter of an area of said surface 2 in contact with said collection material 208 at contact area 209. This feature of the invention ensures that fluid 3 is not "lost" or leaked away from surface 2, thereby diluting the constituents present on the surface and providing an inaccurate reading of constituent concentration. In one embodiment of the invention, collection material 208 may comprise a pad of absorbent fibers for drawing water or solvent 3 into and through collection material 208.

Figure 6:
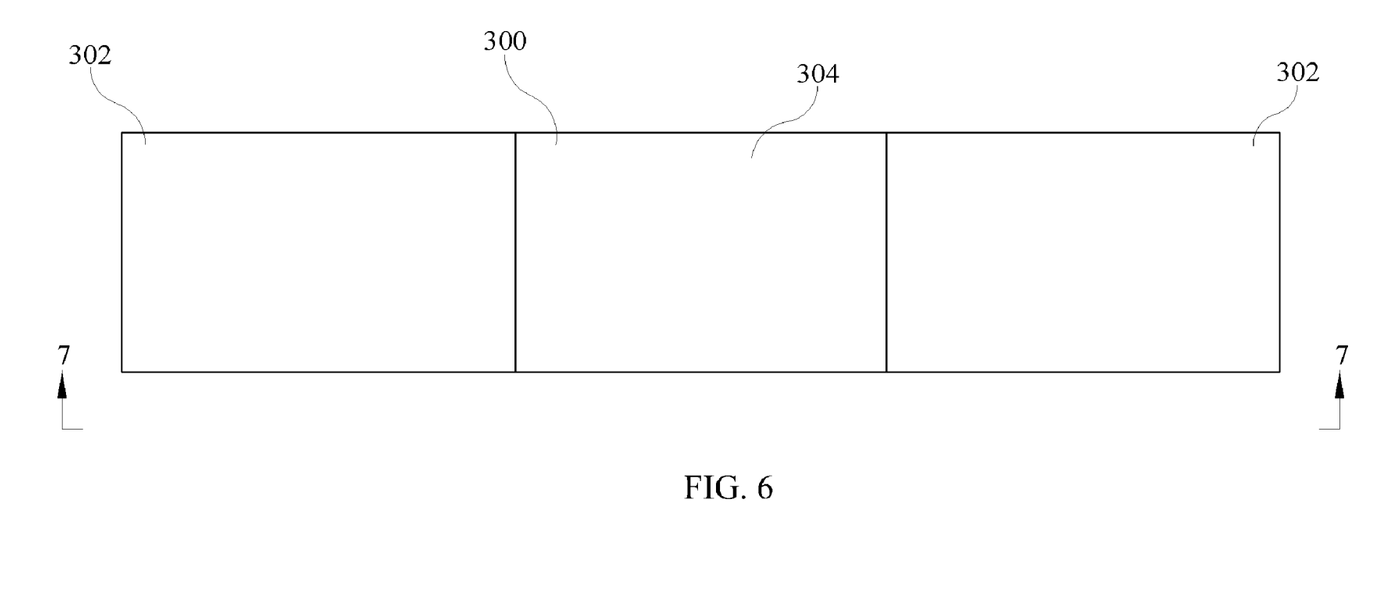
FIG. 6 is a top view of a tack strip in accordance with one embodiment of the present invention.
Figure 7:
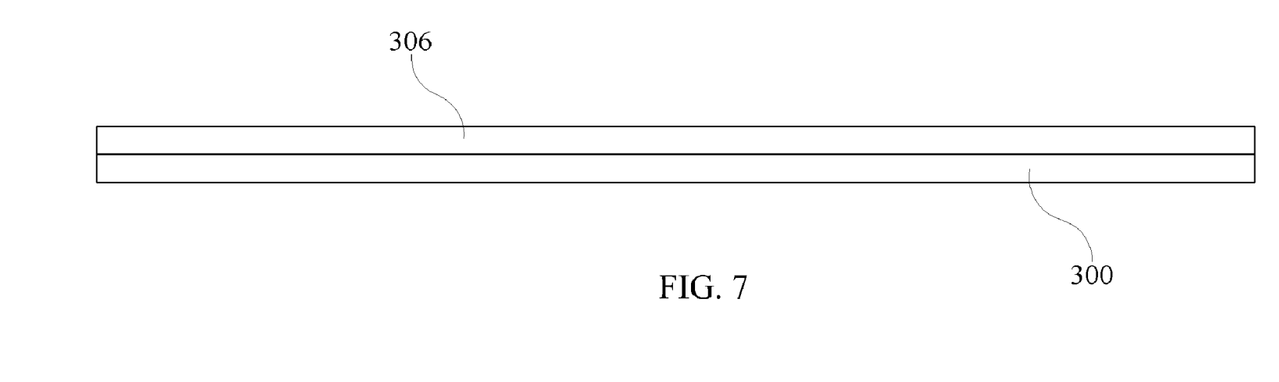
FIG. 7 is a view of a tack strip taken along the line 7-7 in accordance with one embodiment of the present invention.
Figure 8:
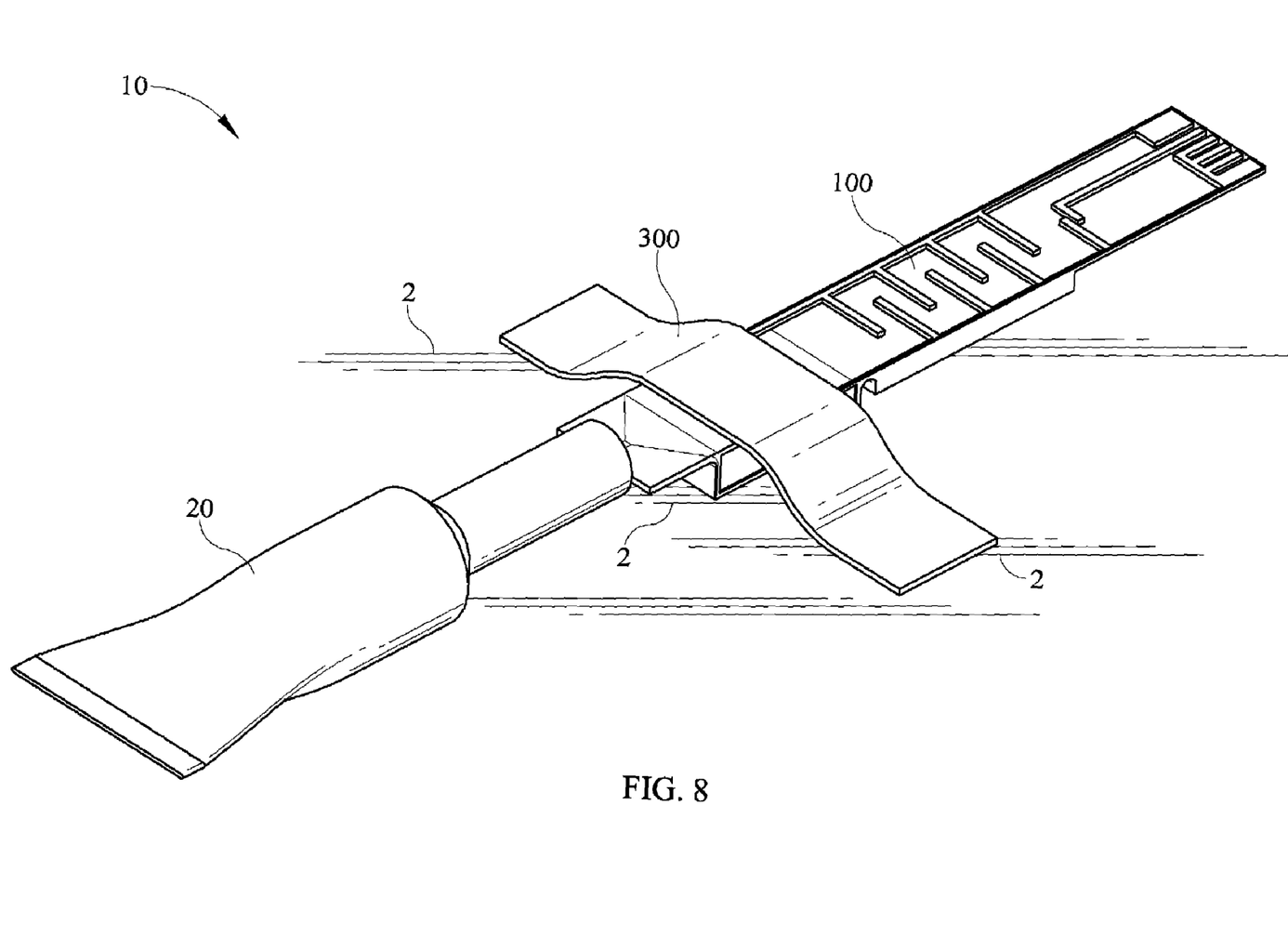
FIG. 8 is an isometric view of a tack strip and a test patch system in accordance with one embodiment of the present invention.

Referring now to FIGS. 6, 7 and 8 the invention further comprises a tack strip 300 which may comprise a flexible strip of plastic material having a layer or coating of adhesive material on one side thereof for contacting both test patch 10 and surface 2, thus securing patch 10 thereto. More specifically, tack strip 300 has two ends 302 that are secured via adhesive to surface 2, while a center section 304 is secured via adhesive to backplane 110 directly over extraction region 200, as shown in FIG. 8. Extraction region 200 contact area 209 is thus forced into intimate contact with surface 2 by tack strip 300, by simply pressing tack strip 300 over backplane 110 (directly over extraction region 200) and onto surface 2. Tack strip 300 is preferably oriented at right angles to a longitudinal axis of test patch 10.

Tack strip 300 is elastic or spring-like, such that it applies pressure across the entire extraction region 200 and maintains contact with surface 2 at end portions 302 such that contact area 209 maintains contact with surface 2. Additionally, since foam layer 204 and support layer 207 act to accurately and evenly distribute force across contact area 209, tack strip 300 provides a simple and efficient mechanism for maintaining contact between collection material 208 and surface 2. One of ordinary skill will recognize that a wide variety of clamping or spring mechanisms may be used in place of tack strip 300 without departing from the scope of the present invention. Additionally, in one embodiment of the present invention, tack strip 300 may be provided with an adhesive release layer 306, for example a thin plastic film, that covers tack strip 300 to protect the adhesive thereon until tack strip 300 is ready to be used.

Extraction region 200 transitions into and connects to collection region 250 where the solution of water 3 (or other solvent) and extracted salts (or other constituent) is collected for further analysis. Collection region 250 comprises a fluid reservoir 252 that may be sized to contain a greater volume of fluid than that contained in extraction region 100. This feature of the present invention permits a positive fluid flow from extraction region 200 to collection region 250, thereby providing more consistent samples. In one embodiment of the invention, reservoir 252 is ten times the volume of the fluid capable of being in extraction region 200. Reservoir 252 is in contact with, and in fluid communication with collection material 208, thereby providing for fluid transport between extraction region 200 and collection region 250. The dimension and surface tension properties of capillary layer 154 and fluid reservoir 252 provide a driving force to pull solvent 3, and thus extracted salts or other constituents, out of collection material 208 into fluid reservoir 252.

In another embodiment of the present invention, reservoir 252 may contain collection material 208 or an equivalent fiber mat collection material to assist fluid flow from extraction region 200 to collection region 250 and to contain the solvent 3 sample to be tested. The fluid 3 collected in reservoir 252 is in contact with an electrical layer 254 that may comprise a substrate 256 having a plurality of electrodes 258 printed or deposited thereon for analyzing solution 3 collected in reservoir 252. Electrical layer 254 may be disposed generally between backplane 110 and reservoir 252 such that electrodes 258 are accessible to connect to a signal generator or reader (not shown). Additionally, in an alternative embodiment of the invention, electrical layer 254 may be printed or deposited directly onto backplane 110 thereby enhancing ease of assembly and reducing material costs. Finally, reservoir 252 and electrical layer 254 may be enclosed by a watertight plastic membrane 260 to facilitate assembly of test patch 10.

In one embodiment of the invention, a portion of electrodes 258 may remain uncovered by membrane 260 to facilitate electrical connections to a reader (not shown).

As best seen in FIG. 1, a capillary channel 270 is provided in backplane 110 and is in contact with reservoir 252 such that fluid 3 flow through capillary channel 270 and across a dye spot 272 deposited in capillary channel 270. Capillary channel 270, dye spot 272, and electrical layer 254 may be covered by a watertight plastic layer 276 through which a hole 274 is bored. Hole 274 permits air to escape while reservoir 252 is filling with water. Dye spot 272 may comprise a small quantity of fluorescent dye, for example. At an end of capillary channel 270 a hole 274 permits air to escape while reservoir 252 is filling with water. Once reservoir 252 is filled with water 3, water is pulled into capillary channel 270 thereby forcing dye from dye spot 272 up the capillary channel. This streak or line of dye thus provides a visual indication to an operator or user that reservoir 252 is full and that test patch 100 is ready to be analyzed or read. In another embodiment of the invention, electrical layer 254 may include additional electrodes 280 that are positioned across capillary layer 270 proximate each other. In this embodiment of the invention, a signal can be provided across electrodes 280 to validate that the capillary channel 270 contains water and thus that test patch 100 is ready for analysis.

In an alternative embodiment of the invention, a flexible wire or similar material may run longitudinally along a substantial length of system 10 to permit portions thereof to be flexed and bent into configurations amenable to surface mounting. For example, ampoule 20 and a portion of transition region 150 may be oriented to ensure water flow to extraction region 200 by simply bending the wire.

In operation, the system is used by inserting ampoule 20 over end 152 of transition region 150 to initiate water flow through capillary layer 154 into extraction region 200. Adhesive release layer 306 is removed and test patch system 10 is secured onto a surface 2 to be tested such that tack strip 300 and collection material 208 are in contact with surface 2. Alternatively, test patch system 10 may be secured to the test surface 2 using tack strip 300 prior to inserting ampoule 20 over end 152 of transition region 150. Water 3 and collected salts flow through capillary layer 154 into collection material 208, thence into reservoir 252. Once dye spot 272 indicates that capillary channel 270 contains fluid, test patch system 10 is removed from the surface, whereupon electrodes 258 are electrically connected to a reader that supplies a known electrical signal thereto and calculates the conductivity of the solution contained in reservoir 252 from the attenuation detected in said signal, as is generally known in the art.

While the present invention has been discussed in the context of measuring salts and the conductivity thereof on a surface being tested, one of ordinary skill will recognize that a variety of printed sensors and electrodes for measuring a plurality of constituents may be employed as an electrical layer 254 in the test patch 100 of the present invention without departing from the scope thereof. As one example, a thermistor may be included in electrical layer 254 to permit for temperature corrections of constituent data taken using the system and method of the present invention. This is particularly useful when the measurement of constituent data is temperature sensitive, or when multiple constituents are being tested.

In a yet further embodiment of the present invention reservoir 252 or transition region 150 may be doped or infused with chemical reagents to selectively react with specific constituents in predetermined chemical reactions. In one embodiment, the reagents may effect a color change in the solvent being used to provide visual indicia of the presence or absence of specific constituents like chlorides. Alternatively the chemical reagent utilized to dope reservoir 252 or transition region 150 may modify the properties of the extracted solution such that test patch 100 measurement is specific to a selected constituent in the extracted solution.

While the present invention has been shown and described herein in what are considered to be the preferred embodiments thereof, illustrating the results and advantages over the prior art obtained through the present invention, the invention is not limited to those specific embodiments. Thus, the forms of the invention shown and described herein are to be taken as illustrative only and other embodiments may be selected without departing from the scope of the present invention, as set forth in the claims appended hereto.

We claim:

1. A test system for taking a sample of a constituent on a surface utilizing a fluid source comprising:
   a transition region having a capillary layer for delivering a fluid from said fluid source;
   an extraction region having a collection material in contact with said surface, said collection material in fluid communication with said capillary layer for receiving said fluid; and
   a collection region having a sensor reservoir therein, said sensor reservoir in fluid communication with said extraction region collection material for delivery of fluid thereto.

2. A test system for taking a sample of a constituent on a surface utilizing a fluid source as claimed in claim 1 comprising:
   a plurality of electrodes in contact with said sensor reservoir for applying an electrical signal thereto and determining conductivity of the fluid contained therein.

3. A test system as claimed in claim 1 comprising:
   at least one watertight layer surrounding said capillary layer of said transition region.

4. A test system as claimed in claim 1 comprising:
   a backplane on which said transition region, said extraction region, and said collection region are secured.

5. A test system as claimed in claim 4 comprising:
   a watertight backplane extending along the length of said system.

6. A test system as claimed in claim 5 comprising:
   a plurality of electrodes in contact with said sensor reservoir for applying an electrical signal thereto and determining conductivity of the fluid contained therein; said electrodes positioned between said sensor reservoir and said backplane.

7. A test system as claimed in claim 4 comprising:
   a fluid transport layer in contact with said collection material and said sensor reservoir for transporting fluid from said collection material to said sensor reservoir.

8. A test system as claimed in claim 1 comprising:
   an extraction region having a closed cell foam layer contacting said collection material to permit said collection material and said foam layer to conform to uneven surfaces.

9. A test system as claimed in claim 8 further comprising:
   a watertight support shim disposed between said collection material and said foam layer to provide even compression of a defined area of said collection material against said surface.

10. A test system as claimed in claim 1 comprising:
    a collection material permitting fluid flow from a front portion thereof to a rear portion thereof and to and from any area of said surface in contact with the collection material, while preventing fluid escaping from the sides of said collection material and from the perimeter of an area of said surface in contact with said collection material.

11. A test system as claimed in claim 10 wherein the flow of said fluid from transition region to collection region is controlled by the capillary and absorbent properties of said transition region capillary layer, said collection material and said sensor reservoir.

12. A test system as claimed in claim 1 further comprising:
    an extraction region having an adhesive layer surrounding a portion of said collection material for securing said system to said surface.

13. A test system as claimed in claim 1 comprising:
    a sensor reservoir having collection material disposed therein for containing fluid therein.

14. A test system as claimed in claim 1 comprising:
    a watertight plastic layer surrounding said collection region thereby preventing fluid from exiting said collection region.

15. A test system as claimed in claim 1 comprising:
    a flexible wire extending substantially the length of said system for orienting said system to said surface.

16. A test system as claimed in claim 1 wherein said reservoir has a fluid volume greater than the fluid volume of said extraction region.

17. A test system as claimed in claim 1 wherein said reservoir has a fluid volume ten times greater than the fluid volume of said extraction region.

18. A test system as claimed in claim 1 comprising:
    an ampoule containing fluid in fluid communication with said capillary layer of said transition region.

19. A test system as claimed in claim 18 wherein said ampoule is a sealed unit that is engaged by a shaped end of said transition region to release said fluid.

20. A test system as claimed in claim 1 wherein said collection material is an absorbent pad of fibers.

21. A test system as claimed in claim 1 wherein said electrodes are disposed on a flexible substrate.

22. A test system as claimed in claim 1 comprising:
    a fluid transport layer in contact with said capillary layer, said collection material, and said sensor reservoir for transporting fluid from said capillary layer to said collection material, and from said collection material to said sensor reservoir.

* * * * *